United States Patent
Cao

(10) Patent No.: US 7,481,121 B1
(45) Date of Patent: Jan. 27, 2009

(54) ORTHODONTIC FORCE MEASUREMENT SYSTEM

(75) Inventor: Heng Cao, Santa Clara, CA (US)

(73) Assignee: Align Technology, Inc., Santa Clara, CA (US)

( * ) Notice: Subject to any disclaimer, the term of this patent is extended or adjusted under 35 U.S.C. 154(b) by 3 days.

(21) Appl. No.: 11/881,528

(22) Filed: Jul. 27, 2007

(51) Int. Cl.
*G01L 1/22* (2006.01)
(52) U.S. Cl. .................................. 73/862.044
(58) Field of Classification Search ............ 73/862.044, 73/862.045; 433/172, 173
See application file for complete search history.

(56) References Cited

U.S. PATENT DOCUMENTS

| | | | |
|---|---|---|---|
| 5,630,717 A | * | 5/1997 | Zuest et al. ............... 433/172 |
| 5,791,350 A | | 8/1998 | Morton |
| 5,885,078 A | * | 3/1999 | Cagna et al. ............... 433/172 |
| 6,120,287 A | | 9/2000 | Chen |

OTHER PUBLICATIONS

Cao, Heng et al., "Applications of Mechanics with Invisalign", *The Invisalign System, Quinstessence Publishing Company*, (2006), 153-161.

* cited by examiner

*Primary Examiner*—Jewel Thompson

(57) ABSTRACT

A method for concurrently measuring a force exerted upon each of a plurality of teeth is disclosed. A dentition crown connecting rod associated with a force gauge is positioned such that a dentition crown coupled to the dentition crown connecting rod may be received within a corresponding cavity of a reference aligner. A measurement aligner is then applied to the dentition crown, wherein the dentition crown is positioned to be received within a corresponding cavity of a reference aligner. A force exerted on the dentition crown by the measurement aligner is then calculated.

26 Claims, 5 Drawing Sheets

ORTHODONTIC FORCE MEASUREMENT SYSTEM

FIELD OF THE INVENTION

The present invention relates generally to the field of orthodontics.

BACKGROUND OF THE INVENTION

Orthodontic treatments involve repositioning misaligned teeth and improving bite configurations for improved cosmetic appearance and dental function. Repositioning is typically accomplished by a dentist or orthodontist (hereinafter practitioner) applying gentle forces by a dental appliance (e.g., braces or positioning appliances) to a patient's teeth over an extended period of time. Due to the limited space within the oral cavity and extensive movements that some teeth must undergo, the teeth will often be moved throughout a series of intermediate patterns to properly arrange the teeth.

Braces comprise a variety of appliances such as brackets, bands, archwires, ligatures, and O-rings. After the brackets are bonded to the teeth, periodic meetings with the treating practitioner are required to allow them to reactively adjust the braces. This generally involves installing different archwires having different force-inducing properties, and/or replacing or tightening existing ligatures.

In contrast, positioning appliances or aligners are comprised of a thin shell of material that generally conforms to a patient's teeth but each appliance provides a teeth receiving cavity geometry that is slightly out of alignment with the initial tooth configuration. Placement of the aligner over the teeth applies controlled forces in specific locations to gradually move the teeth into a new configuration of a predetermined treatment plan. Repetition of this process with successive aligners, each providing a new unique teeth receiving cavity, eventually moves the teeth through a series of intermediate arrangements to a final desired arrangement in accordance with the predetermined treatment plan.

The force that will be generated by braces or an aligner system to teeth can be calculated by finite element analysis modeling. Currently, the systems that exist for obtaining such measurements suffer from issues of inaccuracy and their ability to look at multiple teeth and their movements relative to each other. Thus, it takes much time and effort to obtain a force measurement for multiple teeth within the jaw structure, and any result can rarely be replicated.

SUMMARY

A method for concurrently measuring a force exerted upon each of a plurality of teeth is disclosed. A dentition crown connecting rod associated with a force gauge is positioned such that a dentition crown coupled to the dentition crown connecting rod may be received within a corresponding cavity of a reference aligner. A measurement aligner is then applied to the dentition crown, wherein the dentition crown is positioned to be received within a corresponding cavity of a reference aligner. A force exerted on the dentition crown by the measurement aligner is then calculated.

Figure 1:
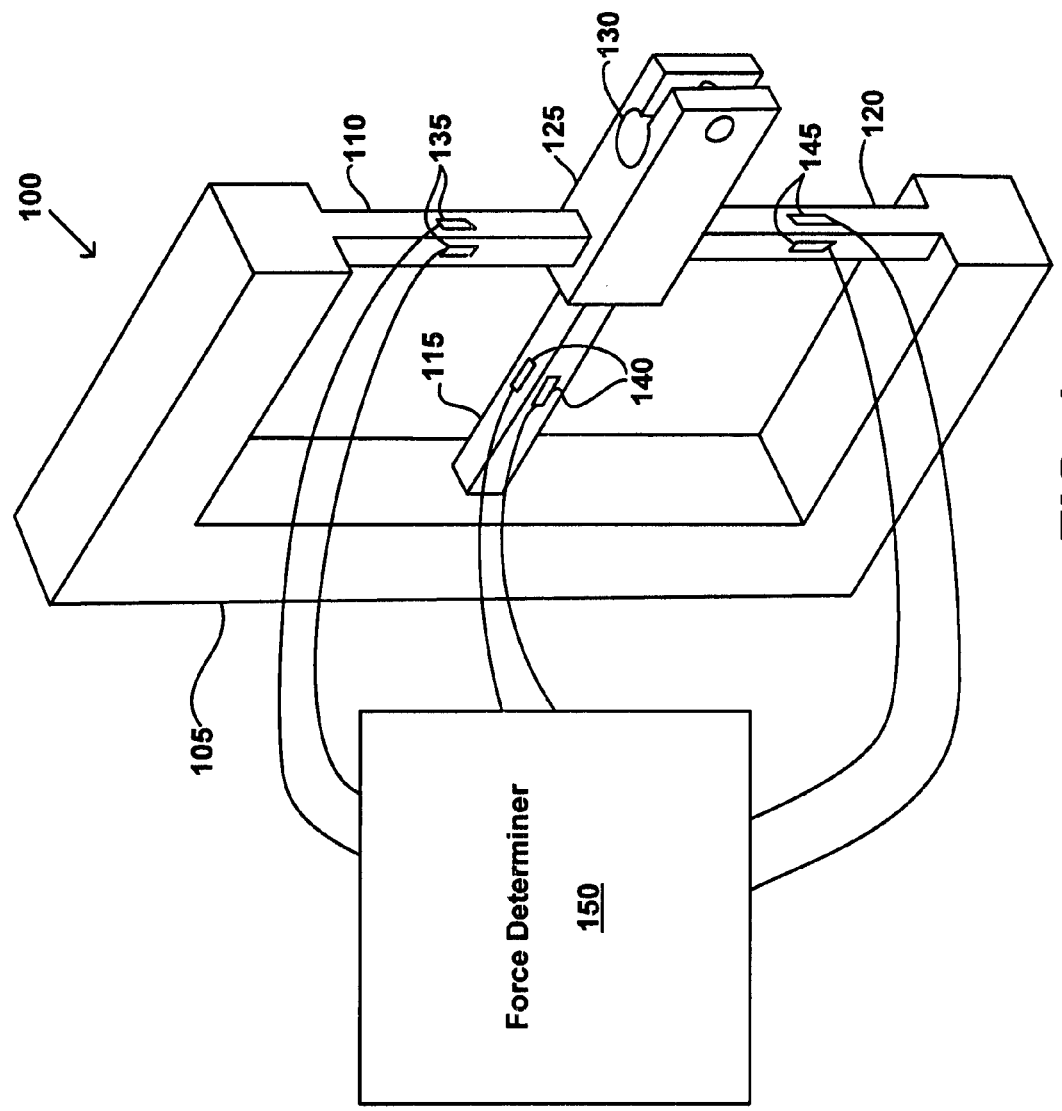
FIG. 1 is a perspective view of a force gauge coupled to a force determiner, according to one embodiment.

The drawings referred to in this description should not be understood as being drawn to scale unless specifically noted.

DETAILED DESCRIPTION OF THE INVENTION

Before the present force gauge tool, force measurement systems and methods are described, it is to be understood that this invention is not limited to particular tools, systems and methods specifically described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

It must be noted that as used herein and in the appended claims, the singular forms "a", "an", and "the" include plural referents unless the context clearly dictates otherwise. Thus, for example, reference to "a tooth" includes a plurality of such teeth, and reference to "the appliance" includes reference to one or more appliances and equivalents thereof known to those skilled in the art, and so forth.

While specific reference may be made to a user, patient, practitioner, or other person using the disclosed tools and systems, and practicing the disclosed methods, it is to be understood that such terms are meant to be inclusive of all such users, unless the context clearly dictates otherwise.

The discussion will begin with an overview of the general process of measuring a force exerted upon an individual tooth, and the limitations of this process. The discussion will then focus on embodiments of the present technology that provide a force gauge for measuring a force exerted upon a tooth, and that provide a force measurement system for concurrently measuring a force exerted upon each of a plurality of teeth. The discussion will then focus on the method for concurrently measuring a force exerted upon each of a plurality of teeth.

Overview

An aligner may be placed on the tooth crown so as to reposition misaligned teeth. This aligner delivers a force to the tooth crown in order to move the tooth to the intended position. A certain amount of force is necessary to move this tooth to its intended position.

Due to the varied size, shape and narrow spacing around each tooth, off-the-shelf force gauges are incapable of being fit into an arrangement to concurrently measure the in vitro force on each tooth in a jaw.

Embodiments of the present technology provide a method for concurrently measuring how much force a dental appliance (e.g., braces or aligner) exerts upon each of a plurality of teeth. For example, a model of a tooth is coupled via a dentition crown connecting rod to a three dimensional force gauge. An aligner is then placed over this tooth model. The force exerted upon the tooth model by the aligner may then be measured by six components of force (x, y, z, a, b, and c, wherein a, b, and c represent the rotation about the X, Y, and Z axis respectively).

By calculating the force exerted upon a tooth by a dental appliance (e.g. aligner, braces) using the disclosed force gauge, it is possible to concurrently determine the force exerted upon each of a plurality of teeth. In this manner, a dental appliance may be tested to determine if it satisfactorily performs its intended function of re-aligning teeth to a pre-determined position. Additionally, new products and new materials for re-aligning teeth may be efficiently tested.

Structure

With reference now to FIG. 1, a perspective view of a force gauge 100 is shown. In this embodiment, force gauge 100 comprises frame 105, beams 110, 115, and 120, fixture 125, and fixture hole 130. Additionally, beams 110, 115, and 120 are configured to have at least one of strain gauges 135, 140, and 145 coupled thereto. Furthermore, FIG. 1 shows strain gauges 135, 140, and 145 coupled to force determiner 150.

The above assembled components enable force gauge 100 to sense a force exerted upon a dentition crown by a dental appliance. For example, a three dimensional model of a tooth is made. This 'dentition crown' (model of a tooth) is coupled to a dentition crown connecting rod. The dentition crown connecting rod is coupled to fixture 125 when inserted into fixture hole 130 and locked into place at a starting or original position. An aligner is then placed over the dentition crown to apply a force to the dentition crown locked into the starting position. The force applied to the dentition crown travels from the dentition crown to the dentition crown connecting rod, and then to fixture 125. This force is then transferred from fixture 125 beam 110, beam 115, and beam 120.

Beams 110, 115, and 120 realize a force causing deformation in the x, y, and z direction, as well as a rotational force (torque) causing deformation in the a, b, and c direction (wherein a, b, and c are rotational forces about the x, y, and z axes, respectively). Sensing this deformation, strain gauges 135, 140, and 145 output a respective voltage to force determiner 150. The voltage output is then recorded, measured, and converted to force measurements by force determiner 150. Consequently, in one embodiment, force gauge 100, as will be described in greater detail in the Operation section herein, enables the measurement of force as exerted by an aligner onto a dentition crown in the x, y, z, a, b, and c direction.

Figure 5:
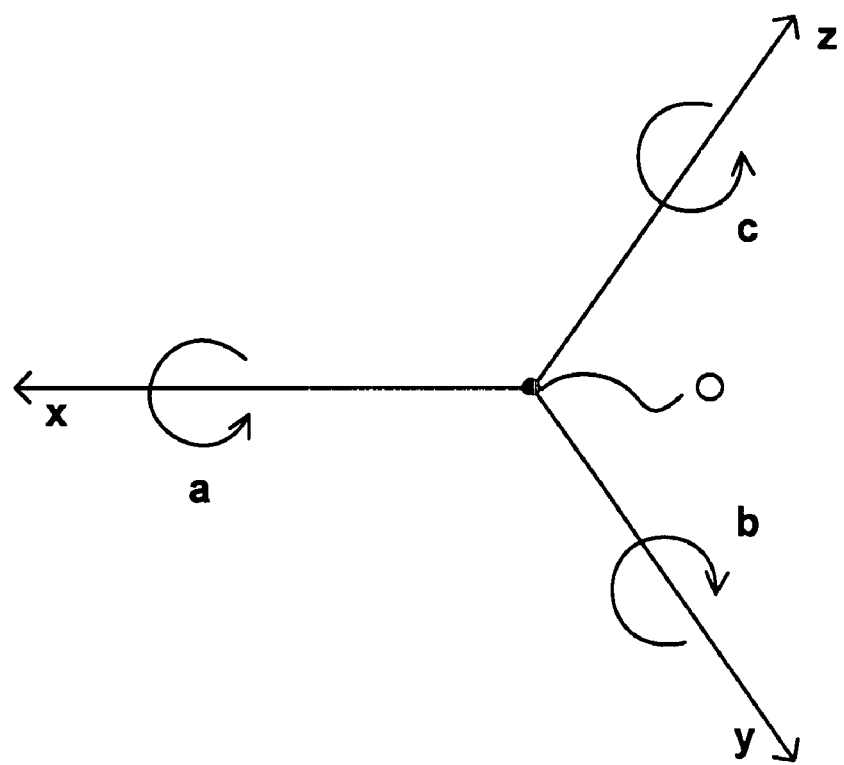
FIG. 5 is a representation of the force gauge coordinate system, with forces x, y, z, a, b, and c, caused by the pulling, compressing and/twisting of beams, whose origin can be fixed at a certain point in three dimensional space.

Referring now to FIG. 5, a representation of a force gauge coordinate system of x, y, and z is shown, whose origin can be fixed at a certain point in three dimensional space. The origin of this force gauge coordinate system is located at the intersection point of beams 110, 115, and 120. Beams 110, 115, and 120 are pulled, compressed and/or torqued in response to a dental appliance being applied to dentition crown 220. Strain gauges 135, 140, and 145, attached to beams 110, 115, and 120 respectively, sense the strain put upon beams 110, 115, and 120, and each output voltage to force determiner 150 proportional to the deformation of the area to which it is attached.

Frame 105 is configured to provide a stable body to which the first end of beam 110, beam 115, and beam 120 is coupled. Additionally, the body of frame 105 may be of an elastic nature, such that frame 105 remains a stable body for the first end of beam 110, beam 115, and beam 120, but may provide enough flexibility to allow for in vitro positioning of force gauge 100.

Figure 2:
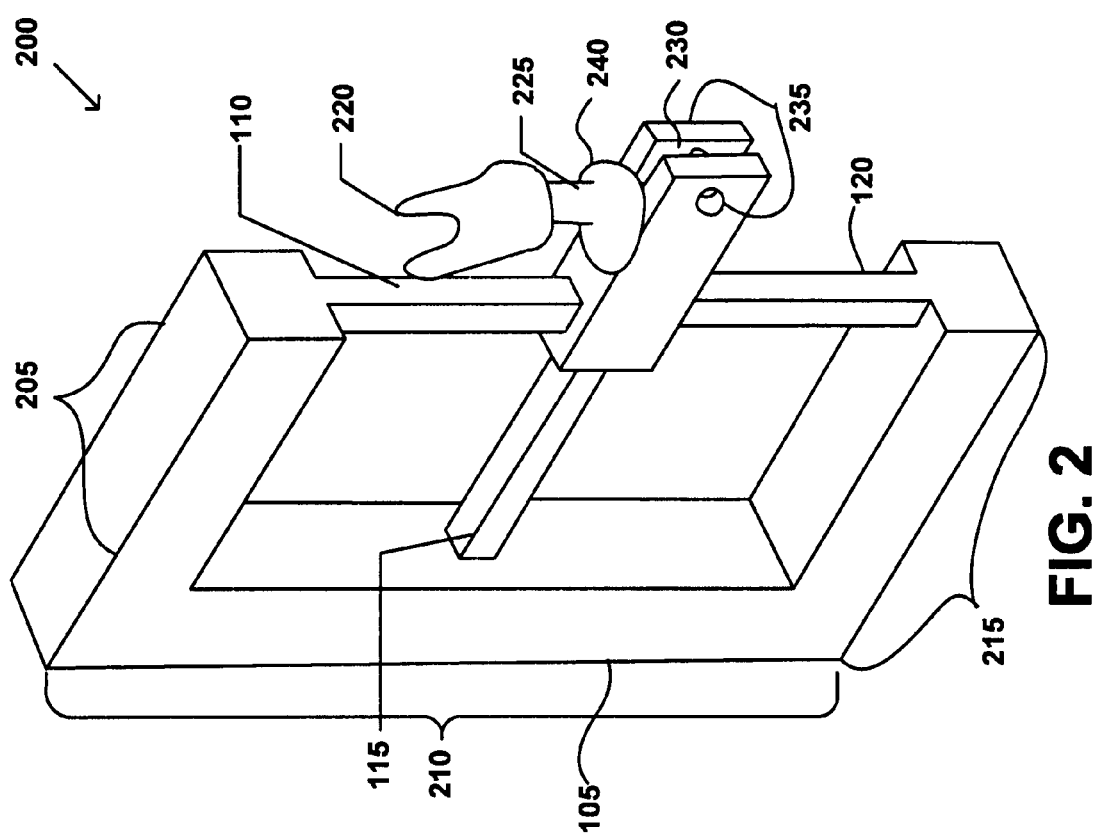
FIG. 2 is a perspective view of a force gauge coupled to a dentition crown connecting rod, according to one embodiment.

With reference now to FIG. 2, the force gauge 100 of FIG. 1 is shown for sensing a force exerted upon dentition crown 220. Fixture 125 is configured to receive dentition crown connecting rod 225 which is coupled to dentition crown 220. Although FIGS. 1 and 2 show force gauge 100 with a plurality of strain gauges 135, 140, and 145 coupled to beams 110, 115, and 120 respectively, it is appreciated that force gauge 100 may have at least one strain gauge coupled to each of beams 110, 115, and 120. Each of the plurality of strain gauges 135, 140, and 145 are configured to sense a force exerted upon the respective beams to which they are coupled. This force was transferred from dentition crown 220 to dentition crown connecting rod 225 to fixture 125, to strain gauges 134, 140, and 145. Consequently, each of plurality of strain gauges 135, 140, and 145 are configured to sense a force exerted by a dental appliance upon dentition crown 220.

FIGS. 1 and 2 display frame 105 as being in a U-shape. However, it is appreciated that frame 105 may be in any shape to which the first end of three beams 110, 115, and 120 may be coupled to frame 105 as well as to fixture 125. Additionally, the three beams must also be configured so as to have a plurality of strain gauges 135, 140, and 145 coupled thereto such that a force exerted upon dentition crown 220 may be sensed. Moreover, the base of frame 105 may partially or wholly be comprised of a type of material which has an attraction to a magnetic table, such as iron or stainless steel.

In an example of the present technology, dentition crown 220 is a three dimensional object, such as a model of a tooth crown, representing any number of sources. For example, dentition crown 220 may be a model of a patient's tooth crown (based upon a digital model), or may be a model of an ideal tooth crown within an arrangement of a plurality of ideal tooth crowns. In this instance, the term 'ideal' refers to a pre-determined desired position for a generic set of teeth. Dentition crown 220 and dentition crown connecting rod 225 are coupled to each other so that both objects are a single body, for force measurement purposes.

Dentition crown 220 and dentition crown connecting rod 225 can be two parts formed using different techniques and then jointed together. In one example, a ceramic dentition crown 220 may be bonded by glue to a stainless steel dentition crown connecting rod 225. The bonding may be removed by removing the glue material. In another example, a stainless steel dentition crown 220 may be welded to a stainless steel dentition crown connecting rod 225. In order to separate these parts, machining off the welding may be necessary.

Strain gauges 135, 140, and 145 may be made out of silicon or any other material which would allow for sensing a force exerted upon dentition crown 220. Moreover, strain gauges 135, 140, and 145 may be one of any number of shapes, simple or complex, including but not limited to: rectangular, square, round, oval or some variation thereof. Strain gauges 135, 140, and 145 may be shear strain gauges configured to consider the angular distortion of an object, such as a beam, under stress. An example of strain gauges 135, 140, and 145 suitable for use in the present technology are sold under the trademark ESB-020™, and are available for purchase from companies such as Measurement Specialties, located at 1000 Lucas Way, Hampton, Va. 23666. Additionally, strain gauges 135, 140, and 145 are attached to beams 110, 115, and 120 and coupled to force determiner 150, respectively, in any manner recognized in the state of the art of applying and using strain gauges.

Force determiner 150 may be comprised of any number of devices configured to calculate a force exerted upon dentition crown 220.

Referring again to the embodiment of FIG. 2, frame 105 has width 205 which is less than length 215, and width 205 which is less than height 210. This configuration enables frame 105 to be placed in close proximity with other frames 105, while still permitting a force to be sensed by strain gauges 135, 140, and 145. For example, if width 205 is greater than length 215, then length would have to be very small in order to couple a plurality of frames 105 to a model of a set of teeth. If the length of frame 105 was small enough to allow each of a plurality of force gauges 100 with widths 205 greater than lengths 215 to be coupled to each of a plurality of adjacent dentition crown connecting rods 225, then there would not be enough space within the size box of frame 105 (description of size box to follow herein) to accommodate beams 110, 115, and 120 as well as strain gauges 135, 140, and 145. Hence, by limiting the dimensions of width 205 to be less than length 215 and height 210, force gauge 100 is enabled to be coupled to each of a plurality of dentition crown connecting rods 225 and to have beams 110, 115, and 120 configured to be coupled to strain gauges 135, 140, and 145.

In another embodiment, any dimension of each of the three beams 110, 115, and 120, is less than a corresponding dimension of frame 105 so that beams 110, 115, and 120 together fit within frame 105 according to force gauge's 100 disclosed configuration. For example, the length of beam 110 is less than length 215 of frame 105. The width of beam 115 is less than width 205 of frame 105. The height of beam 120 is less the height 210 of frame 105. This configuration enables beams 110, 115, and 120 to have a deformation to be sensed by strain gauges 135, 140, and 145.

In an example of the present technology, the combination of all three beams 110, 115, and 120, are within a size box of frame 105. For example, FIG. 1 displays frame 105 as being in a U-shape, with a left side as well as a top and bottom of what could be a rectangular box if a right side were added. A size box of frame 105 would be the result of having closed off the open portion of frame's 105 U-shape. For instance, suppose that an imaginary line was drawn from the outside open edge of the top portion of frame 105 to the outside open edge of the bottom portion of frame 105. The resulting shape, including the side, top, bottom, and imaginary line portion, creates a size box. Beam 110, beam 115, and beam 120 lie fully within this size box.

In yet another embodiment, fixture 125 has a width that is not greater than a width of dentition crown 220 associated with fixture 125. For example, if the dentition crown 220 is four millimeters, then the width of fixture 125 to which dentition crown 220 is attached via dentition crown connecting rod 225 has a width that is not greater than four millimeters. Additionally, fixture 125 also includes a fixture hole 130 configured to receive an associated dentition crown connecting rod 225, and a screw, such that fixture gap 230 may be reduced by tightening a clamp. Fixture hole 130 would be large enough for dentition crown connecting rod 225 to fit within fixture hole 130. A screw is then placed within screw holes 235 such that a bolt may be placed upon the screw and tightened. The tightening of the bolt on the screw forms a clamp, forcing the reduction in fixture gap 230, and thus locking dentition crown connecting rod 225 into place.

In another embodiment, dentition crown connecting rod 225 is positioned vertically, while dentition crown connecting rod 225 is also perpendicular to a horizontal plane of a top surface of a platform. For instance, frame's 105 base is coupled to a platform such that frame 105 does not move when a force is exerted upon dentition crown 220. The platform may be made out of any material that supports frame's 105 immovability when a force is exerted upon dentition crown 220. The platform is configured to stabilize frame 105 of force gauge 100. In one instance, the platform is a magnetic table.

In yet another embodiment, dentition crown connecting rod 225 comprises stopper 240. Stopper 240 is configured to limit downward movement of dentition crown 220. Stopper 240 is also configured to maintain a position of dentition crown 220. By limiting the downward movement and maintaining a position of dentition crown 220, dentition crown 220 is located in a position corresponding to a position of an original digital model of a dentition crown within a jaw. Stopper 240 surrounds connecting rod's 225 circumference. In another embodiment dentition crown connecting rod 225 is configured to couple dentition crown 220 directly to fixture 125.

Figure 3:
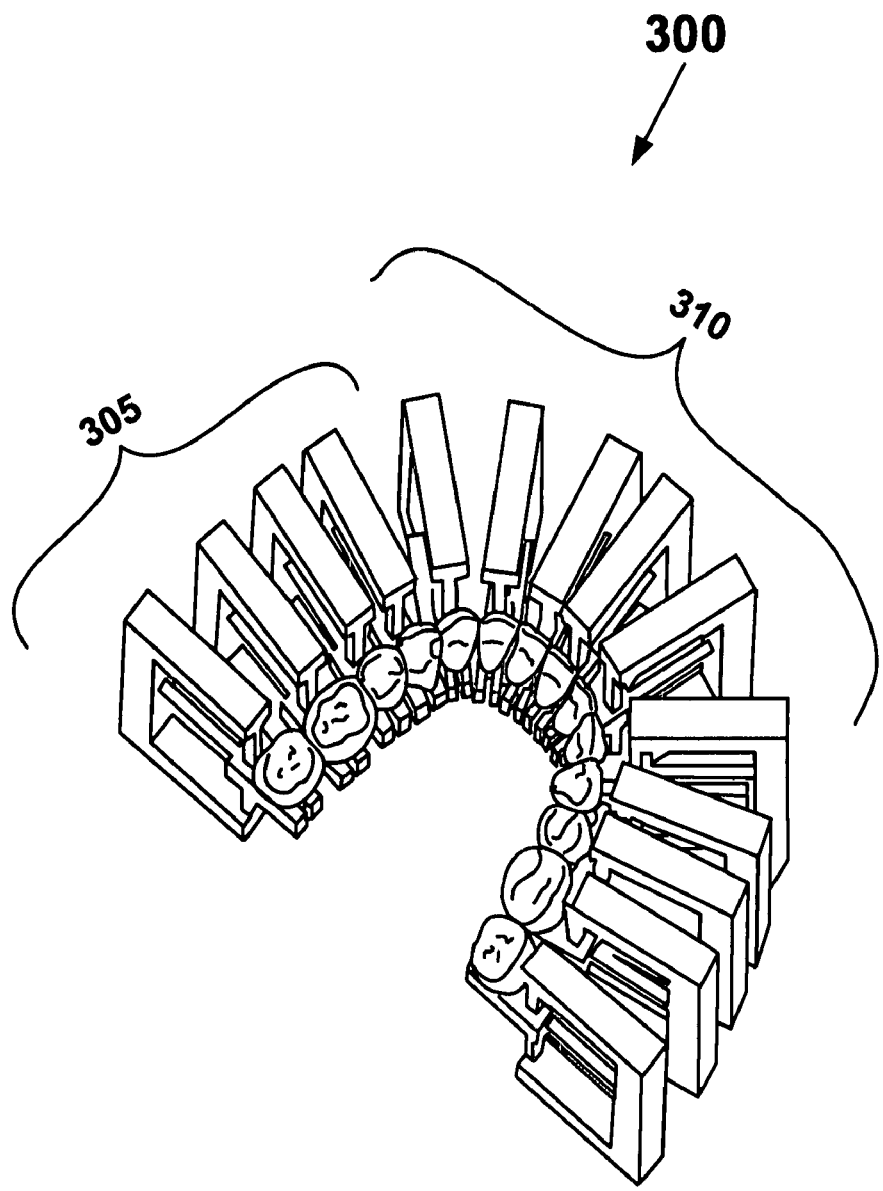
FIG. 3 is a top perspective view of a plurality of force gauges, each force gauge coupled to a dentition crown connecting rod, according to one embodiment.

Referring now to FIG. 3, a perspective view of a force measurement system 300 is shown wherein a plurality of force gauges 100 (see FIGS. 1 and 2) are coupled to dentition crown connecting rod 225. In one embodiment 305, force measurement system 300 includes eight force gauges 100 attached to eight dentition crown connecting rods 225 corresponding to posterior dentition crowns 220. In another embodiment 310, force measurement system 300 includes six force gauges 100 attached to six dentition crown connecting rods 225 corresponding to anterior dentition crowns 220. FIG. 3 shows an example of force gauges 100 varying in their widths to accommodate the varying widths of posterior versus anterior dentition crowns. Additionally, FIG. 3 shows an example of each dentition crown of an entire set of either the upper or lower jaw array of dentition crowns within a jaw, being coupled to force gauges 100. Thus, each of an entire set of upper or lower jaw dentition crowns 220 may be attached to one of a plurality of force gauges 100 and their respective force determiner 150 via dentition crown connecting rods 225, such that the force exerted on each or all of the entire set of lower and/or upper jaw dentition crowns 220 may be measured.

Frame 105 of force measurement system 300 may provide a width 205 that varies with the width of dentition crown 220. The dental appliance may be, but is not limited to the following: a reference aligner, a measurement aligner, and braces. In addition, a platform is coupled to each of a plurality of force gauges 100, wherein a platform is configured to stabilize frame 105 of each of the plurality of force gauges 100.

Using techniques known in the state of the art of orthodontics, a reference aligner is made from a mold, which mold was formed based upon an original digital model of a set of teeth. The reference aligner is used to fit over a set of teeth (either a three dimensional model or a person's set of teeth), and to realign this set of teeth so that they match the original digital model of a set of teeth.

For example, a model of each dentition crown of a set of teeth is formed. Each resulting dentition crown model is then aligned to be in a position matching its corresponding position within a set of teeth. A reference aligner is placed over the aligned dentition crown models. The aligned dentition crown models are then repositioned so as to fit within their corresponding cavity within the reference aligner. Consequently, the reference aligner is used to reposition dentition crown models of a set of teeth so that the set of dentition crown models replicate the positioning of the set of teeth.

A measurement aligner is a variation of the reference aligner described herein, and is formed based upon the original digital model of a set of teeth. However, the measurement aligner represents a mold which is designed to fit a set of teeth (either a three dimensional model or a person's set of teeth) in such a way as to realign the set of teeth to the targeted position of the cavities spaces within the measurement aligner.

Operation

Figure 4:
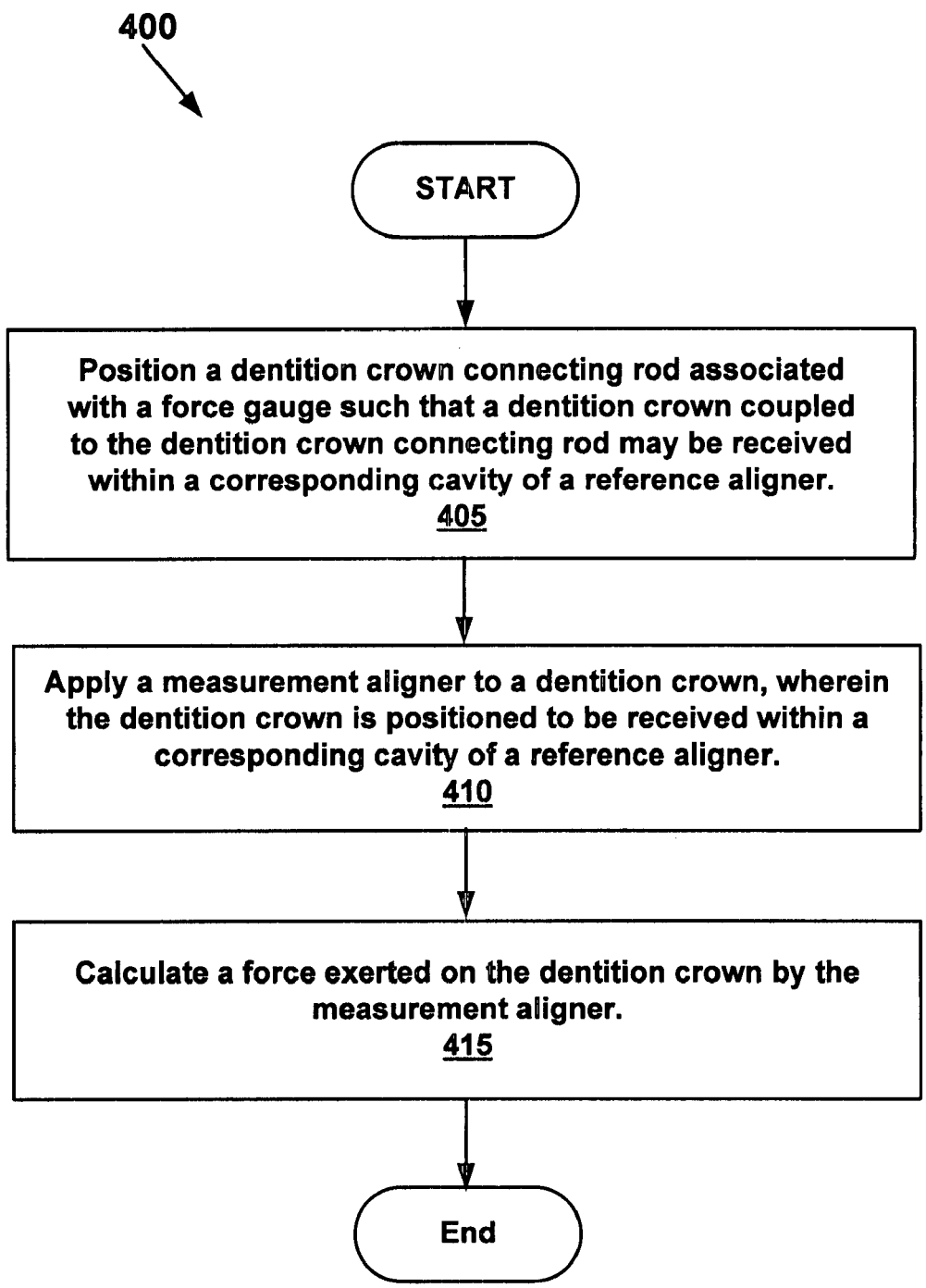
FIG. 4 is a flow diagram of an example method for concurrently measuring a force exerted upon each of a plurality of teeth by a dental appliance, according to one embodiment.

Turning now to FIG. 4, a flowchart 400 is shown of an example method for concurrently measuring a force exerted upon each of a plurality of teeth. With reference to FIGS. 1-3, step 405 recites how a dentition crown connecting rod 225 associated with force gauge 100 is positioned such that dentition crown 220 coupled to dentition crown connecting rod 225 may be received within a corresponding cavity of a reference aligner.

The plurality of dentition crowns 220 may represent an entire set of dentition crowns 220 within a jaw (or a subset of an entire set) such that the force exerted on each of the entire set of dentition crowns 220 within a jaw is concurrently measured.

In one embodiment, positioning dentition crown connecting rod 225 associated with force gauge 100 described herein further comprises: calculating a force exerted upon dentition crown 220 by a reference aligner, wherein the calculated force is shown on a monitor in real time; adjusting a position of dentition crown connecting rod 225 until the force exerted upon dentition crown 220 reaches a tolerance of approximately zero; and in response to the force exerted upon dentition crown 220 reaching a tolerance of approximately zero, locking dentition crown connecting rod 225 into fixture 125.

In one instance, calculating a force exerted upon dentition crown 220 by the reference aligner involves: sensing a strain on two adjacent surfaces of beams 110, 115, and 120 of force gauge 100 by a plurality of strain gauges 135, 140, and 145; recording voltage output; transferring the recorded voltage output to force determiner 150; and utilizing by force determiner 150 the recorded voltage output to calculate the force exerted on dentition crown 220 by a reference aligner.

For example, a reference aligner exerts a force on dentition crown 220 once it is placed upon dentition crown 220. For instance, if a dentition crown 220 is leaning against the reference aligner, then the reference aligner is exerting a force against dentition crown 225. This force is transferred to dentition crown connecting rod 225, which is transferred to fixture 125, which in turn is transferred to beams 110, 115, and 120.

Strain gauges 135, 140, and 145 sense the strain placed upon beams 110, 115, and 120, and output a voltage corresponding to the deformation that it senses. For example, the deformation that strain gauges 135, 140, and 145 sense is due to beams 110, 115, and 120 being twisted, compressed, and/or pulled. This twisting, compressing, and/or pulling may occur in the a, b, c, x, y, and/or z direction. In one instance, strain gauges 135, 140, and 145 are coupled to a voltage measurement circuit as known in the art via wire or some other connection apparatus. It is appreciated that the voltage measurement circuit may be part of force determiner 150 or separate from force determiner 150, while in both instances being communicatively coupled thereto.

The voltage output of strain gauges 135, 140, and 145 is then determined by a voltage measurement circuit. The voltage measurement circuit is communicatively coupled to force determiner 150. Force determiner 150 records the voltage output determined by the voltage meter. Force determiner 150 then utilizes this recorded voltage output to calculate the force exerted on dentition crown 220 by the reference aligner with a standard linear algebra technique.

In one embodiment, a position of dentition crown connecting rod 225 is adjusted (e.g., by moving rod 225 left, right, forward, backward or by rotating the rod within the fixture hole 130 of FIGS. 1 and 2) until the calculated force exerted upon dentition crown 220 reaches a tolerance of approximately zero. Additionally, force gauge 105 may also be moved to aid in achieving a tolerance reading of approximately zero for the force exerted upon dentition crown 220.

In response to a calculated force being exerted upon dentition crown 220 reaching a tolerance of approximately zero, dentition crown connecting rod 225 is locked into fixture 125. For example, dentition crown connecting rod 225 may be locked into fixture 125 by tightening a bolt onto a screw placed in screw holes 235. The tightening of the bolt on the screw forms a clamp, forcing the reduction in fixture gap 230 and also resulting in the locking of dentition crown connecting rod 225 into place. After being locked into place, connecting rod's 225 position may be changed due to the clamping force, which may in turn change the calculated force reading. However, the position of dentition crown connecting rod 225 can still be adjusted by changing the position of frame 105 as it is set on a platform in order to bring the calculated force reading to approximately zero.

Referring again to FIG. 4, step 410 provides that a measurement aligner is applied to dentition crown 220, wherein dentition crown 220 is positioned to be received within a corresponding cavity of a reference aligner. In one embodiment, a pre-set measurement aligner is utilized, wherein the measurement aligner is built to represent the position of each dentition crown 220 incorporating targeted orthodontic movement. For example, while a reference aligner mimics the original position of a tooth or a set of teeth, a measurement aligner mimics the desired position of a tooth or a set of teeth. The reference aligner and the measurement aligner represent two different positions of a tooth or a set of teeth. This difference represents the targeted orthodontic movement.

The measurement aligner is designed by any number of methods which results in an aligner representing the targeted position of a tooth or set of teeth. This may be through computer (digital) methods, manual methods, or a combination thereof. The measurement aligner is placed upon a model of the original positioning of the teeth.

Referring again to FIG. 4 as well as to FIGS. 1-3, step 415 provides that a force exerted on dentition crown 220 by the measurement aligner is calculated. This force is calculated via the method described herein for calculating the force exerted upon dentition crown 220 by the reference aligner.

Furthermore, in one embodiment, the calculated force may be transformed into a tooth coordinate system, wherein the tooth coordinate system is defined based on a geometry of dentition crown 220. For instance, an orthodontic practitioner or an engineer might want to look at a three dimensional viewpoint of the forces exerted on dentition crown 220. However, the calibration matrix obtained via force gauge coordinate system is based upon the strain experienced by beams 110, 115, and 120 and corresponding strain gauges 135, 140, and 145. In other words, while the tooth coordinate system is determined by tooth geometry, the force gauge coordinate system is determined, independent of tooth geometry, by a calibration matrix.

The resulting force calculation from a force exerted by a dental appliance upon dentition crown 220 may not be easily comprehensible to an orthodontic practitioner or an engineer, due to its being designed to be independent of the tooth coordinate system. For example, an orthodontic practitioner is familiar with the tooth coordinate system, which has its own x, y, and z coordinates associated with tooth geometry.

According to technologies within the art, these calculations may be transformed into a three dimensional system, thereby making the force calculations more understandable to some practitioners and engineers.

By calculating the force exerted upon a tooth by a dental appliance (e.g. aligner, braces) using the disclosed force gauge, it is possible to concurrently determine the force exerted upon each of a plurality of teeth. In this manner, a dental appliance may be tested to determine if it satisfactorily performs its intended function of re-aligning teeth to a predetermined position. Additionally, new products and new materials for re-aligning teeth may be efficiently tested. Furthermore, to aid in a practitioner's or engineer's comprehension, the calculated force may be transformed into a tooth coordinate system, wherein the tooth coordinate system is defined based on a geometry of dentition crown 220.

In calculating the force exerted upon dentition crown 220 by the reference aligner using the disclosed force gauge 100, it is possible to concurrently determine the force exerted upon each of a plurality of teeth. In this manner, it is possible to determine the force a measurement aligner delivers to each dentition crown 220. This force measurement enables a cost beneficial method of testing a measurement aligner's ability to satisfactorily perform its intended function.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A force gauge comprising:
    a frame coupled to a first end of a plurality of beams, wherein said frame is configured to provide a stable body to which said first end of each of said plurality of beams is coupled; and
    a fixture coupled to a second end of said plurality of beams, wherein said fixture is configured to receive a dentition crown connecting rod, each of said plurality of beams configured to have at least one strain gauge coupled thereto, said at least one strain gauge configured to sense a force exerted upon a dentition crown when said dentition crown is coupled to said dentition crown connecting rod.

2. The force gauge of claim 1, wherein said force is measured by six components representing the tilt and rotation of an X, Y, and Z axis.

3. The force gauge of claim 1, wherein said plurality of beams is three beams such that said frame is coupled to a first end of each of said three beams and said fixture is coupled to a second end of said each of said three beams.

4. The force gauge of claim 1, wherein said frame further comprises:
    a width less than a length of said frame, and said width less than a height of said frame.

5. The force gauge of claim 1, wherein any dimension of said each of said plurality of beams is less than a corresponding dimension of said frame.

6. The force gauge of claim 1, wherein said plurality of beams are within a size box of said frame.

7. The force gauge of claim 1, wherein said fixture further comprises:
    a width that is not greater than a width of a dentition crown associated with said fixture;
    a fixture hole configured to receive an associated dentition crown connecting rod and a screw such that a fixture gap may be reduced by tightening a clamp.

8. The force gauge of claim 1, wherein said dentition crown connecting rod is vertical, and said dentition crown connecting rod is perpendicular to a horizontal plane of a top surface of a platform, wherein said platform is configured to stabilize said frame of said force gauge.

9. The thin frame force gauge of claim 1, wherein said dentition crown connecting rod further comprises:
    a stopper configured to limit downward movement and to maintain a position of a dentition crown such that said dentition crown is located in said position corresponding to a position of an original digital model of said dentition crown within a jaw.

10. A force measurement system for concurrently measuring a force exerted upon each of a plurality of teeth, said system comprising:
    a plurality of dentition crown connecting rods operatively coupled to a dental appliance;
    a plurality of force gauges, wherein each of said plurality of force gauges is coupled to a plurality of strain gauges, each of said plurality of strain gauges configured to sense a force exerted on each of a plurality of dentition crowns by said dental appliance;
    a force determiner coupled to said each of said plurality of strain gauges, wherein said force determiner is configured to calculate said force exerted on said each of said plurality of dentition crowns by said dental appliance; and
    a platform coupled to said each of said plurality of force gauges, wherein said platform is configured to stabilize a frame of said each of said plurality of force gauges.

11. The force measurement system of claim 10, wherein said force is measured by six components representing the tilt and rotation of an X, Y, and Z axis.

12. The force measurement system of claim 10, wherein said plurality of dentition crowns represent an entire set of dentition crowns within a jaw such that the force exerted on each of said entire set of dentition crowns within a jaw is concurrently measured.

13. The force measurement system as recited in claim 10, wherein each of said plurality of force gauges further comprises:
    a frame coupled to a first end of a plurality of beams, wherein said frame is configured to provide a stable body to which said first end of a plurality of beams is coupled.

14. The force measurement system as recited in claim 13, wherein said plurality of beams is three beams such that said frame is coupled to a first end of each of said three beams and a fixture is coupled to a second end of said each of said three beams.

15. The force measurement system as recited in claim 10, wherein said plurality of strain gauges is coupled to each of a plurality of beams.

16. The force measurement system as recited in claim 10, wherein each of said plurality of force gauges further comprises:
    a fixture coupled to one of said plurality of dentition crown connecting rods, and said fixture coupled to a second end of a plurality of beams, wherein said fixture is configured to receive said one of said plurality of dentition crown connecting rods.

17. The force measurement system as recited in claim 16, wherein said fixture further comprises:
- a width that is not greater than a width of a dentition crown associated with said fixture; and
- a fixture hole configured to receive an associated dentition crown connecting rod and a screw such that a fixture gap may be reduced by tightening a clamp.

18. The force measurement system as recited in claim 10, wherein said each of said plurality of dentition crown connecting rods further comprises:
- a stopper configured to limit downward movement and to maintain a position of a dentition crown such that said dentition crown is located in said position corresponding to a position of an original digital model of said dentition crown within a jaw.

19. The force measurement system as recited in claim 10, wherein said platform is a magnetic table.

20. A method for concurrently measuring a force exerted upon each of a plurality of teeth, said method comprising:
- positioning a dentition crown connecting rod associated with a force gauge such that a dentition crown coupled to said dentition crown connecting rod may be received within a corresponding cavity of a reference aligner;
- applying a measurement aligner to said dentition crown, wherein said dentition crown is positioned to be said received within a corresponding cavity of a reference aligner; and
- calculating a force exerted on said dentition crown by said measurement aligner.

21. The method of claim 20, wherein said dentition crown connecting rod is a plurality of dentition crown connecting rods.

22. The method of claim 21, wherein said plurality of dentition crowns represent an entire set of dentition crowns within a jaw such that the force exerted on each of said entire set of dentition crowns within a jaw is concurrently measured.

23. The method of claim 20, wherein said positioning a dentition crown connecting rod associated with said force gauge such that a dentition crown coupled to said dentition crown connecting rod may be received within a corresponding cavity of a reference aligner further comprises:
- calculating said force exerted upon said dentition crown by said reference aligner, wherein said calculated force is shown on a monitor in real time;
- adjusting a position of said dentition crown connecting rod until said calculated force exerted upon said dentition crown reaches a tolerance of approximately zero; and
- in response to said calculated force exerted upon said dentition crown reaching said tolerance of approximately zero, locking said dentition crown connecting rod into fixture.

24. The method of claim 20, wherein said applying a measurement aligner to said dentition crown, wherein said dentition crown of said dentition crown is positioned to be said received within a corresponding cavity of a reference aligner further comprises:
- utilizing a measurement aligner, wherein said measurement aligner represents a position of each said dentition crown incorporating targeted orthodontic movement.

25. The method of claim 20, wherein said calculating a force exerted on said dentition crown by said measurement aligner further comprises:
- sensing a strain on two adjacent surfaces of each beam of said force gauge by a strain gauge;
- recording voltage output;
- transferring said recorded voltage output to a force determiner;
- utilizing by said force determiner said recorded voltage output to calculate said force exerted on said dentition crown by said measurement aligner.

26. The method of claim 20, further comprising:
- transforming said calculated force to a tooth coordinate system, wherein said tooth coordinate system is defined based on a geometry of said dentition crown.

\* \* \* \* \*